(12) United States Patent
Wu et al.

(10) Patent No.: US 10,842,505 B2
(45) Date of Patent: Nov. 24, 2020

(54) SURGERY DEVICE FOR OSTEOTOMY (71) Applicant: A Plus Biotechnology Company Limited, New Taipei (TW)

(72) Inventors: Kai-Hsing Wu, Taipei (TW); Hsiang Wei Lo, New Taipei (TW); Chu An Luo, Yunlin County (TW); Chun-Ming Chen, New Taipei (TW); Ping Sheng Yu, Taipei (TW)

(73) Assignee: A PLUS BIOTECHNOLOGY COMPANY LIMITED, New Taipei (TW)

( * ) Notice: Subject to any disclaimer, the term of this patent is extended or adjusted under 35 U.S.C. 154(b) by 267 days.

(21) Appl. No.: 15/680,235

(22) Filed: Aug. 18, 2017

(65) Prior Publication Data

US 2018/0049749 A1 Feb. 22, 2018

(30) Foreign Application Priority Data

Aug. 19, 2016 (TW) .............................. 105126498 A
Aug. 10, 2017 (TW) .............................. 106127173 A (51) Int. Cl.
*A61F 5/00* (2006.01)
*A61B 17/15* (2006.01)

(52) U.S. Cl.
CPC .......... *A61B 17/151* (2013.01); *A61B 17/155* (2013.01); *A61B 17/157* (2013.01)

(58) Field of Classification Search
CPC combination set(s) only.
See application file for complete search history.

(56) References Cited

U.S. PATENT DOCUMENTS

2008/0262500 A1* 10/2008 Collazo ................ A61B 17/152
606/88

* cited by examiner

*Primary Examiner* — Sameh R Boles
(74) *Attorney, Agent, or Firm* — Chih Feng Yeh; Huntington IP Consulting Co., Ltd.

(57) ABSTRACT

The present invention provides a surgery device for osteotomy comprises a first body component, a second body component. The first body component has a side guide edge and an upper guide edge for forming a cutting track. The second body component has a lower guide edge disposed below the upper guide edge. A guide groove is formed between the upper guide edge and the lower guide edge for guiding the saw blade to cut. The upper guide edge has a first correcting perforation. The lower guide edge has a second correcting perforation. There is a regulative angle between a first hole axis of the first correcting perforation and a second hole axis of the second correcting perforation. Compared to the prior art, the present invention can improve the efficiency and accuracy of the surgery.

3 Claims, 9 Drawing Sheets

SURGERY DEVICE FOR OSTEOTOMY

BACKGROUND OF THE INVENTION

Field of the Invention

The present invention relates to a surgery device for osteotomy. More specifically, it is related to a surgery device for performing osteotomy and tailor-made for the patient.

Description of the Invention

The knee is one of the most powerful joints in the body to withstand external forces. Most people if the knee had sports injuries or the age was in the middle-aged stage, are likely to cause articular cartilage wear resulting in a symptom of the knee-joint pain. The activity of daily life is reduced. This is the cause of degenerative joint disease.

Past common treatment is to implant the artificial joint to replace the original knee. But in order to implant artificial joints need to remove a large number of articular surface from femur, tibia and patella to provide the fixation of metal and polymer implants. Due to the wear of the implant, the duration of the artificial joint replacement is up to twenty years, but often complicated by postoperative infection, osteolysis and osteoporosis. Resulting in the possibility of a second operation. Furthermore, some of the early patients with degenerative joint disease, in fact, are only the cartilage wear of the medial articular surface. It is not necessary to remove entire articular surface by artificial joint replacement. High tibial osteotomy is usually performed in patients with medial degenerative joint disease.

High tibial osteotomy is performed by cutting an opening in the patient's proximal tibia of the knee on the medial side. And then open the opening to fill the artificial bone. Finally, to be fixed by bone plates and bone needles at the same time. To correct the biomechanical axis of the patient's calf knee. Since cut the bone and adjust the angle in the medial proximal tibia only, so any large amount of bone will not be removed. For the patients with knee-joint pain caused by the cartilage of the medial articular surface, it is a good way for surgical treatment.

However, high tibial osteotomy requires cutting an opening in the proximal tibia. The cutting position, direction and depth, the high of the opening and other procedures are required a careful assessment before surgery. At present, during the operation, the clinician decided that the above-mentioned parameters of the osteotomy often only by the X-ray machine and their personal experience. But the biomechanical axis of the calf knee in each patient with degenerative joint disease is different. The above parameters are also different for each patient. Considering the above-mentioned individual different conditions, the personal differences of the calf knee biomechanical axis in the design of surgical instruments must be considered as well.

SUMMARY OF THE INVENTION

In view of the foregoing problems, the present invention provides a surgery device for osteotomy. It is used to guide a saw blade to perform high tibial osteotomy of tibia, but not limited to, the surgery device for osteotomy can be used for other bones, such as: femur, fibula, humerus, ulna, radius, clavicle, scapula and so on. The tibia is described in the preferred embodiment of the present invention. The exterior design has a feature that can assist the clinician to determine the cutting position, direction and depth, the high of the opening and other procedures precisely. The opening of the tibia after the operation of the present invention will have the accuracy of cutting and the efficiency of the implementation. Each device is tailored to the patient.

The present invention provides a surgery device for osteotomy. The surgery device for osteotomy is used to guide a saw blade to perform high tibial osteotomy of tibia, but not limited to, it can also be applied to other bones. The aforementioned tibia is defined as a first cutting position and a second cutting position by the surgery device for osteotomy. The surgery device for osteotomy comprises: a first body component, a second body component, and a plurality of fixed slots. Wherein the first body component is disposed above the first cutting position and has a side guide edge, an upper guide edge and a first correcting perforation, the first correcting perforation being provided on the upper guide edge; the second body component is disposed below the first cutting position or below the upper guide edge and has a lower guide edge and a second correcting perforation. The lower guide edge is disposed below the upper guide edge. The second correcting perforation is provided on the lower guide edge. The surfaces of the first body component and the second body component have the plurality of fixed slots for fixing the surgery device for osteotomy to the surface of the tibia.

Wherein a guide groove is formed between the upper guide edge and the lower guide edge for guiding the saw blade to the first cutting position. The side guide edge is used to guide the saw blade to the second cutting position. The upper guide edge, the lower guide edge and the side guide edge are employed to form the cutting track. The saw blade cuts the tibia according to the first cutting position and the second cutting position, thereby operating high tibial osteotomy. There is a regulative angle between the first hole axis of the first correcting perforation and the second hole axis of the second correcting perforation. In high tibial osteotomy, a gap of the osteotomy has a preoperative planning correction angle. When the open angle of the gap of the osteotomy is the same as that of the preoperative planning correction angle, the first hole axis of the first correcting perforation and the second hole axis of the second correcting perforation will coincide.

In another embodiment of the present invention, the first correcting perforation is connected to the first body component by a first bar; the second correcting perforation is connected to the second body component by a second bar.

In another embodiment of the present invention, the surgery device for osteotomy further comprises a correction shaft guide component disposed on the surface of the second body component. It comprises a third bar extending to the rear of the second cutting position or the rear of the guide groove and a third correcting perforation. The third correcting perforation is fitted with the preoperative correction axis for high tibial osteotomy as a shaft when the tibia is opened. By using a bone needle as a correction axis in advance, it is nailed to the preoperative planning position of the shaft on the outside of the tibia. When opening the surgical gap, the user can ensure that the rotation axis is the same as the preoperative planning. When the saw blade has reached the pre-planned cutting depth, it will be blocked by the bone needle on the correction axis to ensure the depth of cutting and improve the accuracy of the operation. In addition, the pre-drilled holes can disperse the stress to avoid the fracture of the lateral flare of tibia when opening the gap.

The present invention also provides a surgery device for osteotomy that is used to guide a saw blade to perform high tibial osteotomy of tibia. The aforementioned tibia is defined as a first cutting position and a second cutting position by the surgery device for osteotomy. The surgery device for osteotomy comprises: a first body component, a second body component and a plurality of fixed slots. Wherein the first body component is disposed above the first cutting position and has a side guide edge, an upper guide edge and a first correcting perforation, the first correcting perforation is connected to the first body component by a first bar. The second body component is disposed below the first cutting position or below the upper guide edge and has a lower guide edge and a second correcting perforation. The lower guide edge is disposed below the upper guide edge. The second correcting perforation is connected to the second body component by a second bar. The surfaces of the first body component and the second body component have the plurality of fixed slots for fixing the surgery device for osteotomy to the surface of the tibia.

Wherein a guide groove is formed between the upper guide edge and the lower guide edge for guiding the saw blade to the first cutting position. The side guide edge is used to guide the saw blade to the second cutting position. The upper guide edge, the lower guide edge and the side guide edge are used to form the cutting track. The saw blade cuts the tibia according to the first cutting position and the second cutting position, thereby operating high tibial osteotomy. There is a regulative angle between the first hole axis of the first correcting perforation and the second hole axis of the second correcting perforation. In high tibial osteotomy, a gap of the osteotomy has a preoperative planning correction angle. When the open angle of the gap of the osteotomy is the same as that of the preoperative planning correction angle, the first hole axis of the first correcting perforation and the second hole axis of the second correcting perforation will coincide.

In an embodiment of the present invention, the surgery device for osteotomy further comprises a correction shaft guide component disposed on the surface of the second body component. It comprises a third correcting perforation extending to the rear of the second cutting position. The third correcting perforation is fitted with the preoperative correction axis for high tibial osteotomy as a shaft and ensuring the depth of the cut when the tibia is opened.

Compared with the conventional technique, the surgery device for osteotomy is manufactured by three-dimensional printing (3D printing) according to the patient's skeletal data collected before the operation and evaluating the optimal surgical cutting position. The device itself can fit the patient's tibia fully. The surgeon can perform the first cutting position under the guide groove specified by the device. The guide groove allows the surgeon to perform the operation accurately. It also provides a reference for calculating the angle and depth of cutting. The side guide edge provides the surgical reference of the surgeon at the second cutting position. In addition to improving the surgery itself, the present invention also standardizes the implementation of the surgeon's operation.

DETAILED DESCRIPTION

Some preferred embodiments of the present invention will now be described in greater detail. However, it should be recognized that the preferred embodiments of the present invention are provided for illustration rather than limiting the present invention.

In addition, the present invention can be practiced in a wide range of other embodiments besides those explicitly described, and the scope of the present invention is not expressly limited except as specified in the accompanying claims. The layout of components may be more complicated in practice.

Furthermore, the greater number or lesser number mentioned in the present specification is included in the number itself. It is to be understood that this specification discloses certain methods and processes for carrying out the functions, there are a variety of structures related to the disclosed structures that perform the same function. The above-mentioned structures generally achieve the same result.

Hereinafter, preferred embodiments of the present invention will be described in detail to fully illustrate the features, spirit and advantages of the present invention.

Figures 1A, 1B:
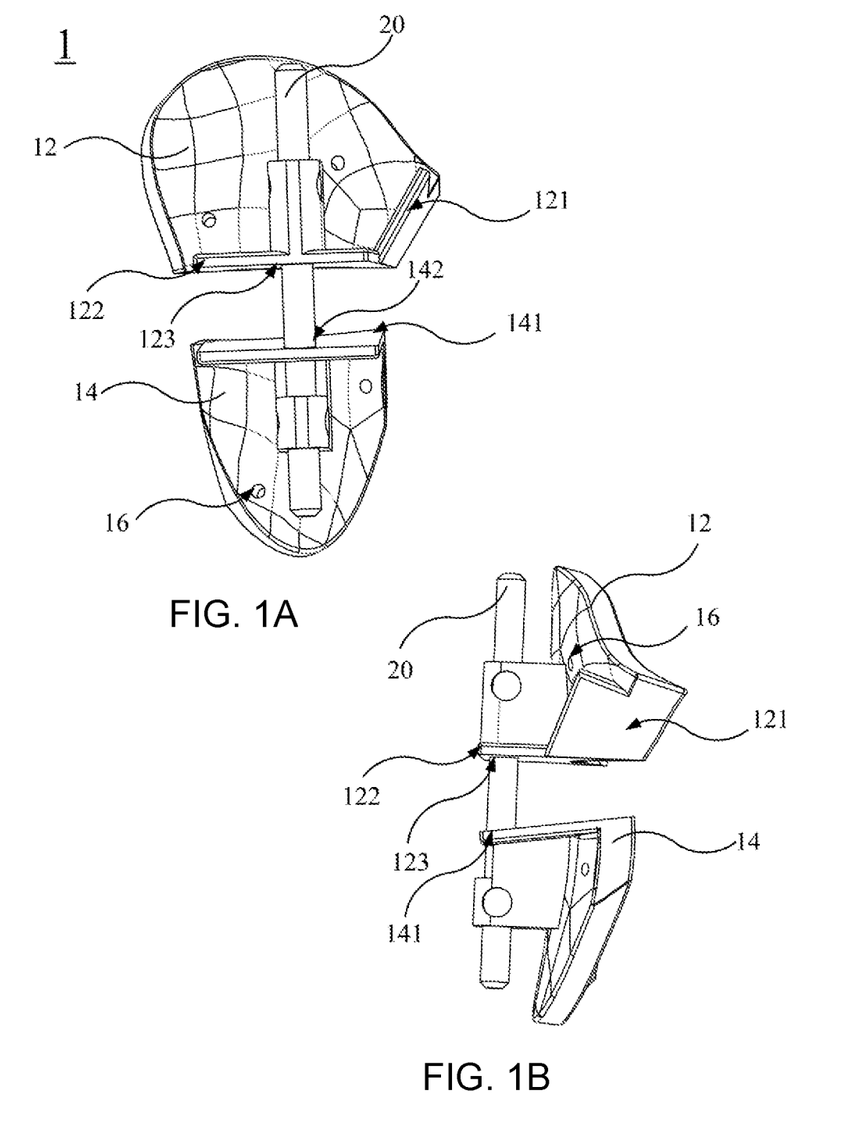
FIG. 1A illustrates a front view of an embodiment of the present invention when implemented.
FIG. 1B illustrates a side view of an embodiment of the present invention when implemented.
Figure 2:
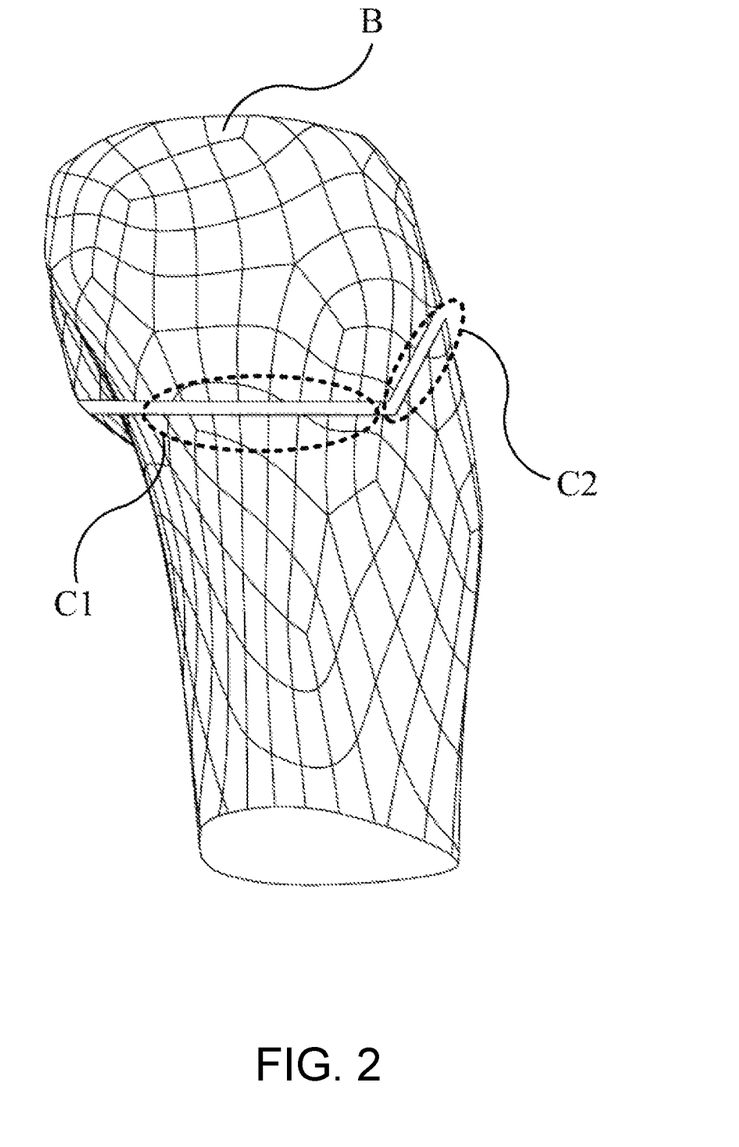
FIG. 2 illustrates the position at which the tibia is to be cut when the present invention is practiced.

Please refer to FIG. 1A, FIG. 1B and FIG. 2. FIG. 1A illustrates a front view of an embodiment of the present invention when implemented. FIG. 1B illustrates a side view of an embodiment of the present invention when implemented. FIG. 2 illustrates the position at which the tibia is to be cut when the present invention is practiced.

The present invention provides a surgery device for osteotomy 1 which can be used in various osteotomy, correction or reduction surgery. The surgery device for osteotomy 1 can be used for various bones of the human body, such as: tibia B, femur D, fibula, humerus, ulna, radius, clavicle, scapula, etc., but not limited to. In the present embodiment, it is applied to guide a saw blade to perform high tibial osteotomy of a tibia B. The tibia B is defined as a first cutting position C1 and a second cutting position C2 by the surgery device for osteotomy 1. The surgery device for osteotomy 1 comprises: a first body component 12, a second body component 14, and a plurality of fixed slots 16. Wherein the first body component 12 is disposed above the first cutting position C1 and has a side guide edge 121 and an upper guide edge 122. The second body component 14 is disposed below the first cutting position C1 or below the upper guide edge 122 and has a lower guide edge 141. The lower guide edge 141 is disposed below the upper guide edge 122. The surfaces of the first body component 12 and the second body component 14 have the plurality of fixed slots 16. The surgery device for osteotomy 1 is fixed on the surface of the tibia B by inserting a plurality of fixing pins and fixed bone needles 40 in the plurality of fixed slots 16.

Wherein the upper guide edge 122 and the lower guide edge 141 extend outwardly from the first body component 12 and the second body component 14, respectively. A guide groove 50 is formed between the upper guide edge 122 and the lower guide edge 141 for guiding the saw blade to the first cutting position C1. The side guide edge 121 is used to guide the saw blade to the second cutting position C2. The upper guide edge 122, the lower guide edge 141 and the side guide edge 121 are used to form the cutting track. The saw blade cuts the tibia B according to the first cutting position C1 and the second cutting position C2, thereby operating high tibial osteotomy.

Figure 3A:
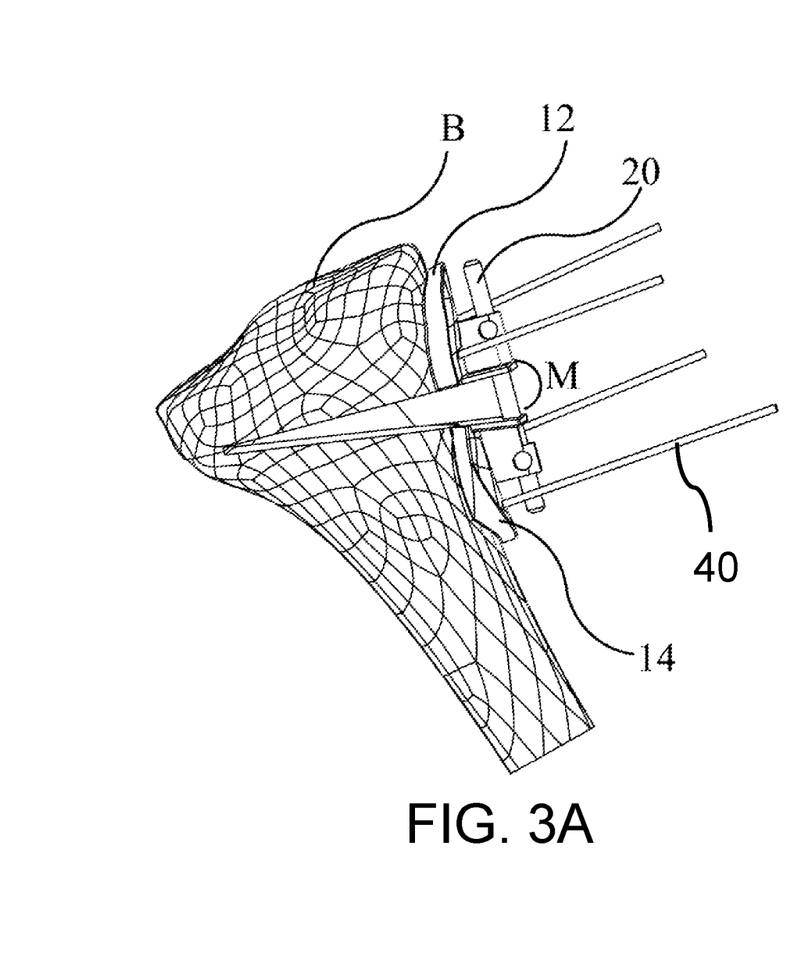
FIG. 3A illustrates a back view of an embodiment of the present invention when implemented in a tibia.
Figure 3B:
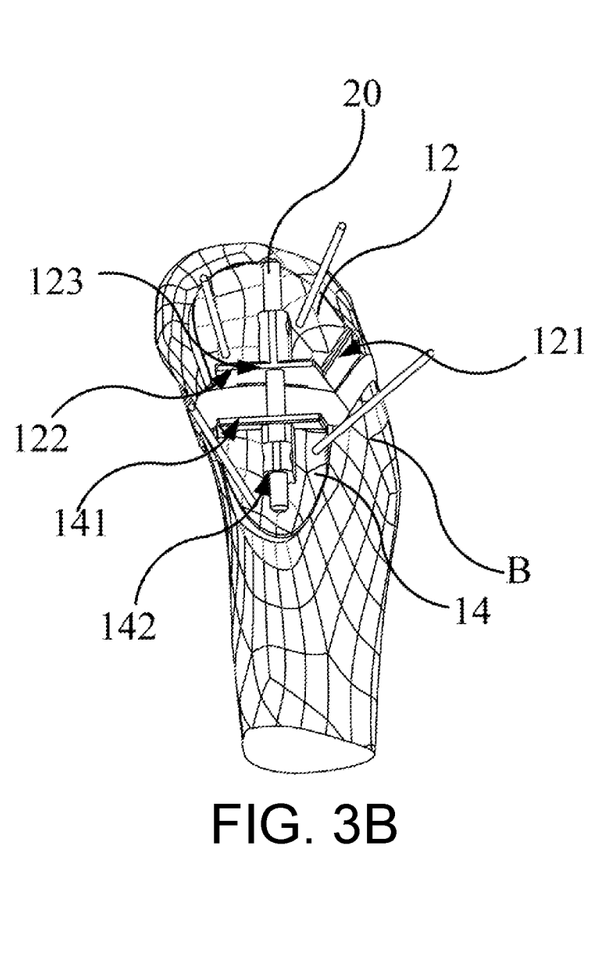
FIG. 3B illustrates a side view of an embodiment of the present invention when implemented in a tibia.

Please refer to FIG. 3A and FIG. 3B. FIG. 3A illustrates a back view of an embodiment of the present invention when implemented in a tibia. FIG. 3B illustrates a side view of an embodiment of the present invention when implemented in a tibia. In an embodiment of the present invention, the first body component 12 further comprises a first correcting perforation 123. The first correcting perforation 123 is provided on the upper guide edge 122. The second body component 14 further comprises a second correcting perforation 142. The second correcting perforation 142 is provided on the lower guide edge 141. In the present invention, the first correcting perforation 123 and the second correcting perforation 142 are designed to confirm the angle at which the tibial opening is opened in high tibial osteotomy. For this reason, there is a regulative angle L between the first hole axis A1 of the first correcting perforation 123 and the second hole axis A2 of the second correcting perforation 142 (the hole axes A1, A2 and the regulative angle are plotted in FIG. 5). In high tibial osteotomy, a gap of the osteotomy has a preoperative planning correction angle M. When the tibia B is opened by the first body component 12 and the second body component 14 with the correction angle M, the first hole axis A1 of the first correcting perforation 123 and the second hole axis A2 of the second correcting perforation 142 can coincide. An alignment bar 20 is passed through the first correcting perforation 123 and the second correcting perforation 142 to ensure the correction angle. Firstly, the size of the aforementioned correction angle is based on the correction angle M that the tibia B needs to open in high tibial osteotomy. Secondly, the angle between the axis of the first correcting perforation and the axis of the second correcting perforation is determined according to the desired correction angle M and it is made. The alignment bar 20 can be inserted between the first correcting perforation 123 and the second correcting perforation 142 only when the tibia B is opened at a preoperative planned correction angle by the first body component 12 and the second body component 14.

Figure 4A:
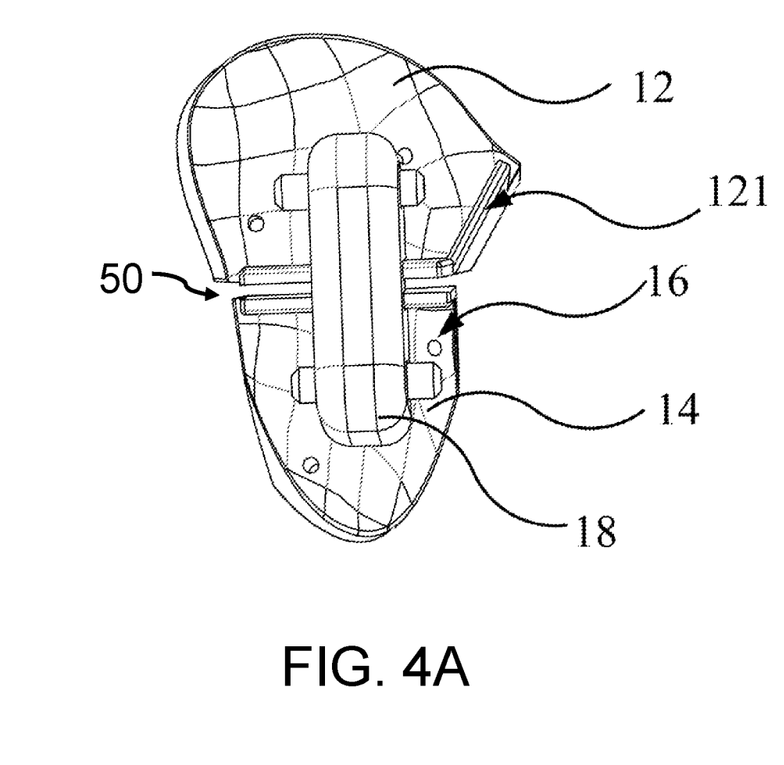
FIG. 4A illustrates a front view of an embodiment of the present invention before implementation.
Figure 4B:
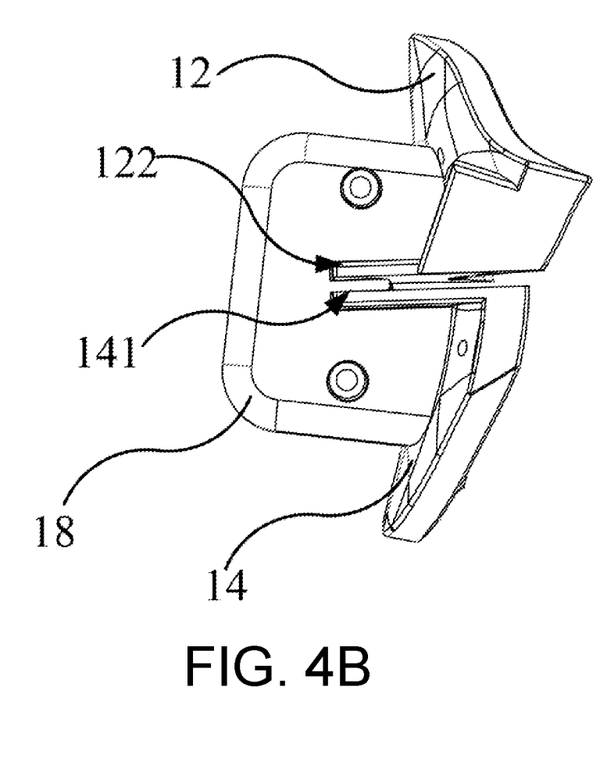
FIG. 4B illustrates a side view of an embodiment of the present invention before implementation.

Please refer to FIG. 4A and FIG. 4B. FIG. 4A illustrates a front view of an embodiment of the present invention before implementation. FIG. 4B illustrates a side view of an embodiment of the present invention before implementation. In one embodiment of the present invention, the first body component 12 and the second body component 14 are made of a 3D printing. Since the first body component 12 and the second body component 14 need to be matched with each other to be applied to the operation. So, the surgery device for osteotomy 1 further comprises a fixing component 18. Before the first body component 12 and the second body component 14 are not in use, the fixing component 18 combines the first body component 12 and the second body component 14 with each other to ensure that there is sufficient area to attach the bone surface. The first body component 12 and the second body component 14 are fixed to the patient's tibia before the first body component 12 and the second body component 14 are used for high tibial osteotomy, and then the fixing component 18 is removed. However, the present invention is not limited to this, the first body component 12 and the second body component 14 may be manufactured in an integrally formed manner. At this time, there is a connecting part between the upper guide edge 122 and the lower guide edge 141, the fixing component 18 is not necessary. When the operation is performed, the surgeon can directly cut the connecting part with the bone saw.

Figure 5:
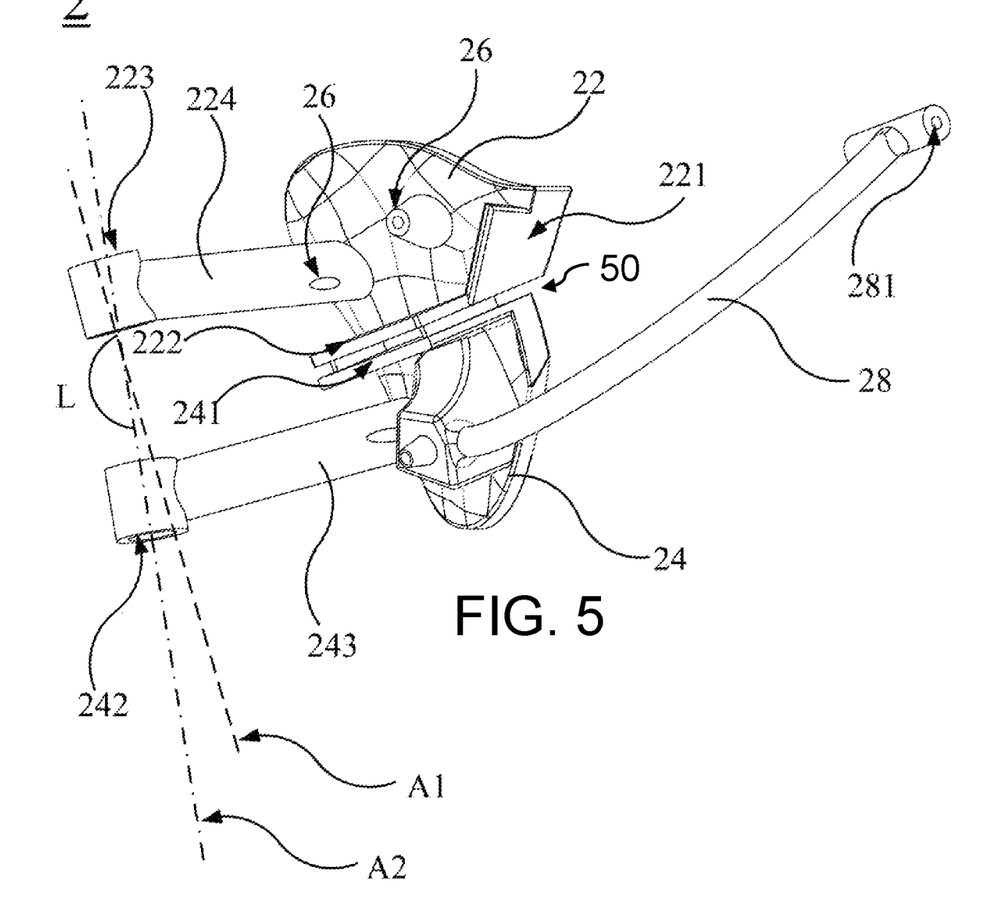
FIG. 5 illustrates another embodiment of the present invention.
Figure 6:
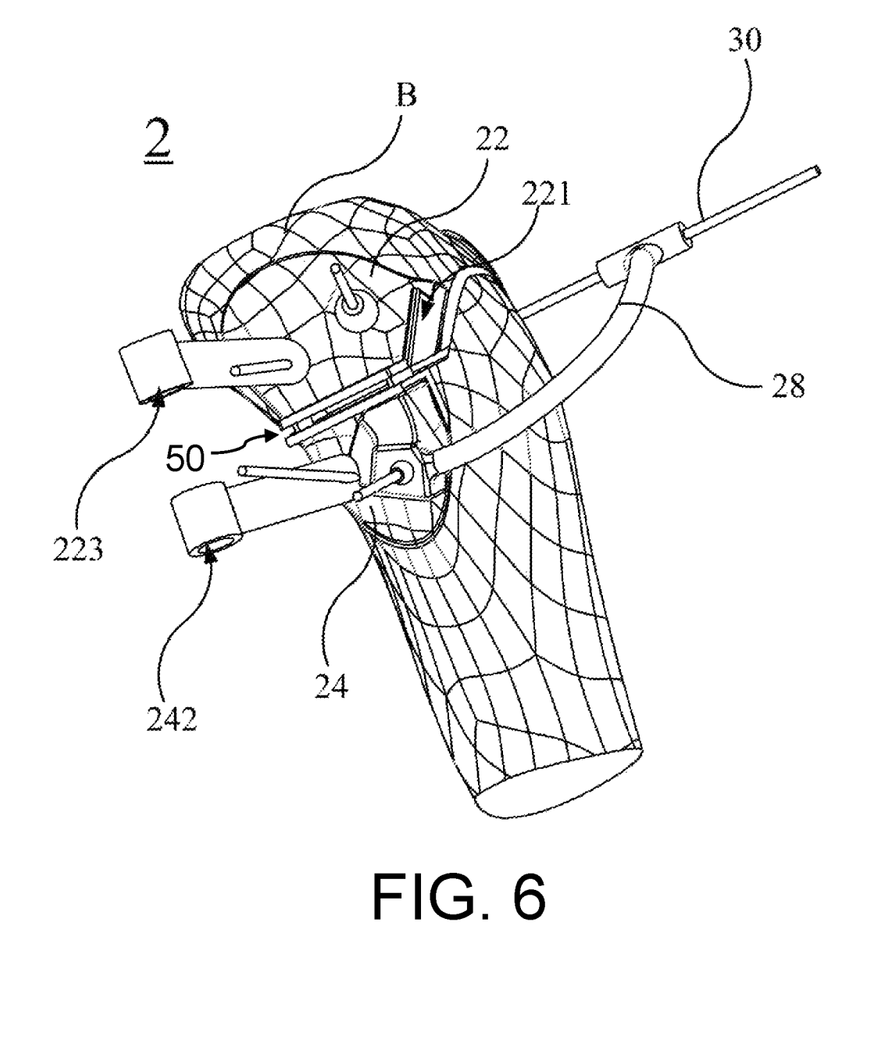
FIG. 6 illustrates another embodiment of the present invention when implemented.

Please refer to FIG. 5 and FIG. 6. FIG. 5 illustrates another embodiment of the present invention. FIG. 6 illustrates another embodiment of the present invention when implemented.

The present invention further provides a surgery device for osteotomy 2 which can be used in various osteotomy, correction or reduction surgery. The surgery device for osteotomy 2 can be used for various bones of the human body, such as: tibia B, femur D, fibula, humerus, ulna, radius, clavicle, scapula, etc., but not limited to. In the present embodiment, it is applied to guide a saw blade to perform high tibial osteotomy of a tibia B. The tibia B is defined as a first cutting position C1 and a second cutting position C2 by the surgery device for osteotomy 2. The surgery device for osteotomy 2 comprises: a first body component 22, a second body component 24, a plurality of fixed slots 26 and a correction shaft guide component 28. In this embodiment, the first body component 22 and the second body component 24 are connected by a connecting part. When the operation is performed, the surgeon can directly cut the connecting part with the bone saw, but not limited to. The first body component 22 and the second body component 24 can be directly used without using the connecting part. In addition, the first body component 22 and the second body component 24 may be connected in other forms.

Wherein the first body component 22 is disposed above the first cutting position C1 and has a side guide edge 221, an upper guide edge 222 and a first correcting perforation 223. The first correcting perforation 223 is connected to the first body component 22 by a first bar 224. The second body component 24 is disposed below the first cutting position C1 or below the upper guide edge 222 and has a lower guide edge 241 and a second correcting perforation 242. The lower guide edge 241 is disposed below the upper guide edge 222. A guide groove 50 is formed between the upper guide edge 222 and the lower guide edge 241. The second correcting perforation 242 is connected to the second body component 24 by a second bar 243. The surfaces of the first body component 22 and the second body component 24 have the plurality of fixed slots 26. The surgery device for osteotomy 2 is fixed on the surface of the tibia B by inserting a plurality of fixing pins and fixed bone needles 40 in the plurality of fixed slots 26. A correction shaft guide component 28 is disposed on the surface of the second body component 24, it comprises a third correcting perforation 281 extending to the rear of the second cutting position C2 or the rear of the guide groove 50. The third correcting perforation 281 is fitted with the preoperative correction axis 30 for high tibial osteotomy as a shaft when the tibia B is opened. By using a bone needle as a correction axis 30 in advance, it is nailed to the preoperative planning position of the shaft on the outside of the tibia, when opening the tibia B, the user can ensure that the rotation axis of the tibia B is the same as the preoperative planning. When the saw blade has reached the pre-planned cutting depth, it will be blocked by the bone needle on the correction axis 30 to ensure the depth of cutting and improve the accuracy of the operation. In addition, pre-drilled holes can disperse the stress to avoid the fracture of the lateral flare of tibia B when opening the gap. The correction shaft guide component 28 and the second body component 24 are integrally formed or combined.

Wherein the upper guide edge 222 and the lower guide edge 241 extend outwardly from the first body component 22 and the second body component 24, respectively. A guide groove 50 is formed between the upper guide edge 222 and the lower guide edge 241 for guiding the saw blade to the first cutting position C1. The side guide edge 221 is used to guide the saw blade to the second cutting position C2. The upper guide edge 222, the lower guide edge 241 and the side guide edge 221 are used to form the cutting track. The saw blade cuts the tibia B according to the first cutting position C1 and the second cutting position C2, thereby operating high tibial osteotomy.

In the present invention, the first correcting perforation 223 and the second correcting perforation 242 are designed to confirm the angle at which the tibial opening is opened in high tibial osteotomy. For this reason, there is a regulative angle L between the first hole axis A1 of the first correcting perforation 223 and the second hole axis A2 of the second correcting perforation 242. In high tibial osteotomy, a gap of the osteotomy has a preoperative planning correction angle. When the tibia B is opened by the first body component 22 and the second body component 24 with the correction angle, the first hole axis A1 of the first correcting perforation 223 and the second hole axis A2 of the second correcting perforation 242 can coincide. An alignment bar 20 is passed through the first correcting perforation 223 and the second correcting perforation 242 to ensure the correction angle. Firstly, the size of the aforementioned regulative angle L is based on the correction angle that the tibia B needs to open in high tibial osteotomy. Secondly, the size of the regulative angle L is determined according to the desired correction angle and it is made. The alignment bar 20 can be inserted between the first correcting perforation 223 and the second correcting perforation 242 only when the tibia B is opened at a preoperative planned correction angle by the first body component 22 and the second body component 24.

Figure 7:
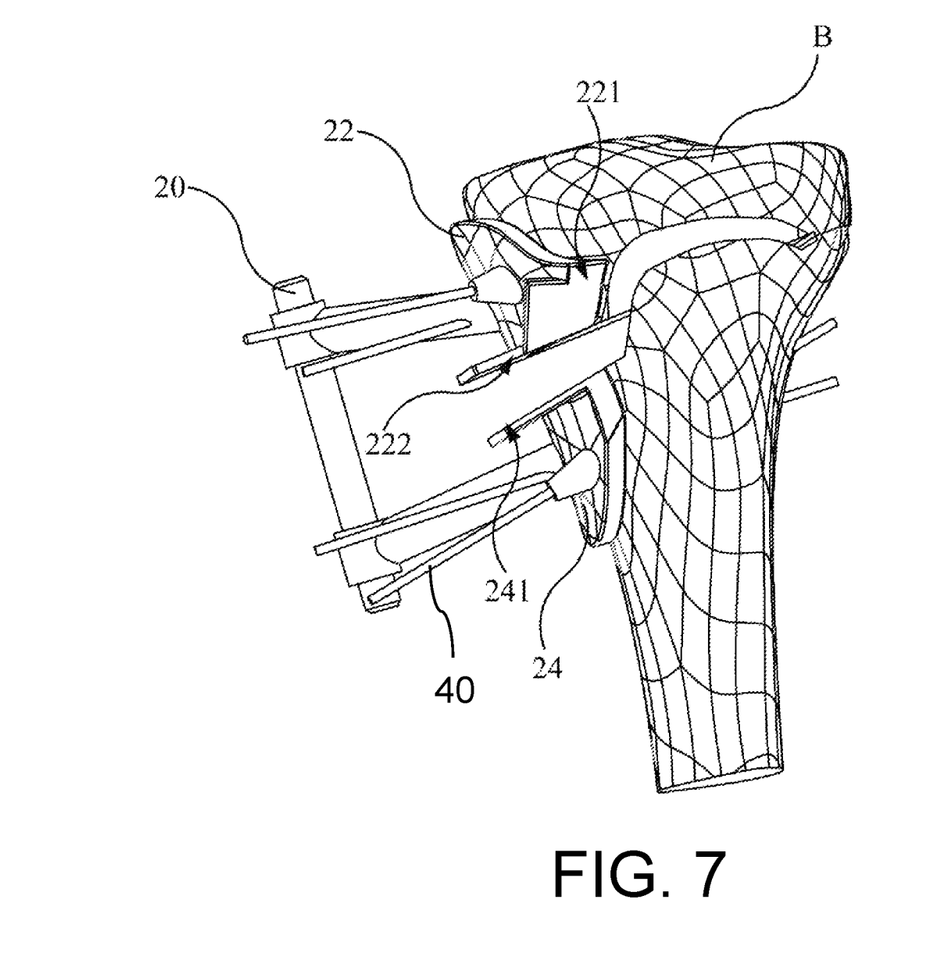
FIG. 7 illustrates a front view of another embodiment of the present invention when implemented.

Please refer to FIG. 2, FIG. 3A, FIG. 3B and FIG. 7. Hereby explain how to use the present invention to perform high tibial osteotomy. In FIG. 2, the surgery devices for osteotomy 1, 2 attached to the tibial position are located in the calf of human body and close to the knee on the medial side of the proximal end. However, the scope of its attachment is not limited to this, it can also be attached to other positions of the other bones. In other words, the picture shows the positive side of FIG. 2 is pointing to the inside of human body. The left side of FIG. 2 points to the back of human body. FIG. 3A and FIG. 3B correspond to the surgery device for osteotomy 1. FIG. 7 illustrates a front view of another embodiment of the present invention when implemented and corresponds to the surgery device for osteotomy 2.

The present invention of the surgery devices for osteotomy 1, 2 are based on the tibial image information provided by patients with degenerative joint disease before surgery. The model of tibia B was established using computer software. The position of the first cutting position C1 and the second cutting position C2 is determined according to the model of tibia B. The overall structure of the surgery devices for osteotomy 1, 2 are tailored. Wherein the surgery devices for osteotomy 1, 2 are designed to be able to fully fit the surface of the patient's tibia B, and then the three-dimensional printing technique is used to construct an integrally formed or combined solid instrument.

When the surgery devices for osteotomy 1, 2 are arranged on the surface of patient's tibia, the surgeon inserts the saw blade and starts cutting according to the first cutting position C1 guided by the upper guide edge 122, 222 and the lower guide edge 141, 241 of the surgery devices for osteotomy 1, 2. The surgeon can use the upper guide edges 122, 222 and the lower guide edges 141, 241 as a reference for the calculation of the depth of cut. In another way, make a mark on the saw blade, the user can use the naked eye to confirm whether the depth of the saw blade cut into the tibia B reached the preset depth.

The saw blade is cut to a predetermined depth and cut along the upper guide edge 122, 222 and the lower guide edge 141, 241 to the inside of the human body. Cut off part of the tibia B. Along the second cutting position C2 guided by the side guide edges 121, 221 to cut out an oblique incision. After the incision is cut, the first cutting position C1 of the tibia B is opened to the correction angle M of preoperative planning in the case where the surgery devices for osteotomy 1, 2 are fixed to the tibia B. The alignment bar 20 is then inserted through the first correcting perforations 123, 223 and the second correcting perforations 142, 242. After confirming the correction angle of the surgical incision of the tibia B, the gap can be fixed to complete the operation.

Figure 8A:
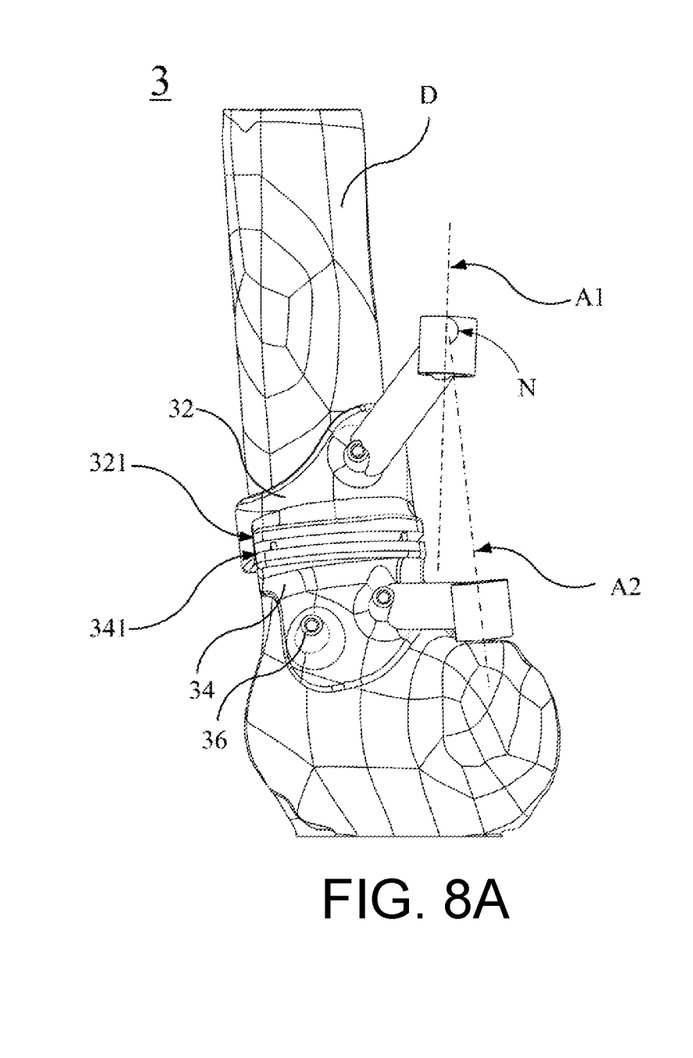
FIG. 8A illustrates a side view of the other embodiment of the present invention when implemented.
Figure 8B:
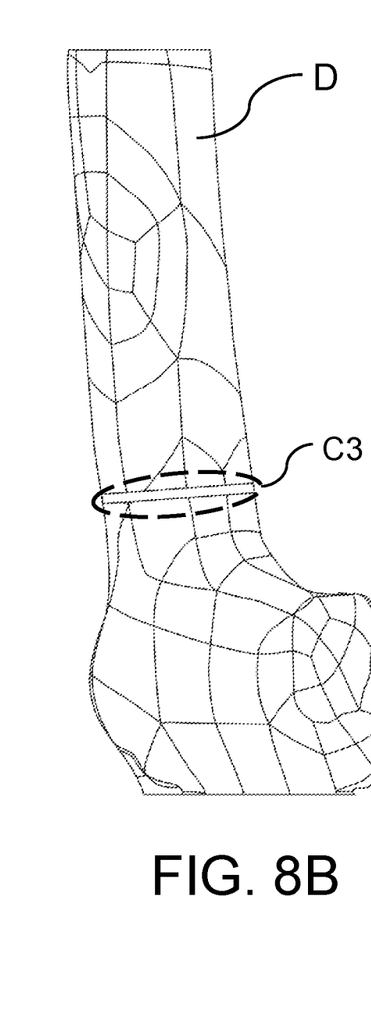
FIG. 8B illustrates the position at which the femur is to be cut when the present invention is practiced.
Figure 9A:
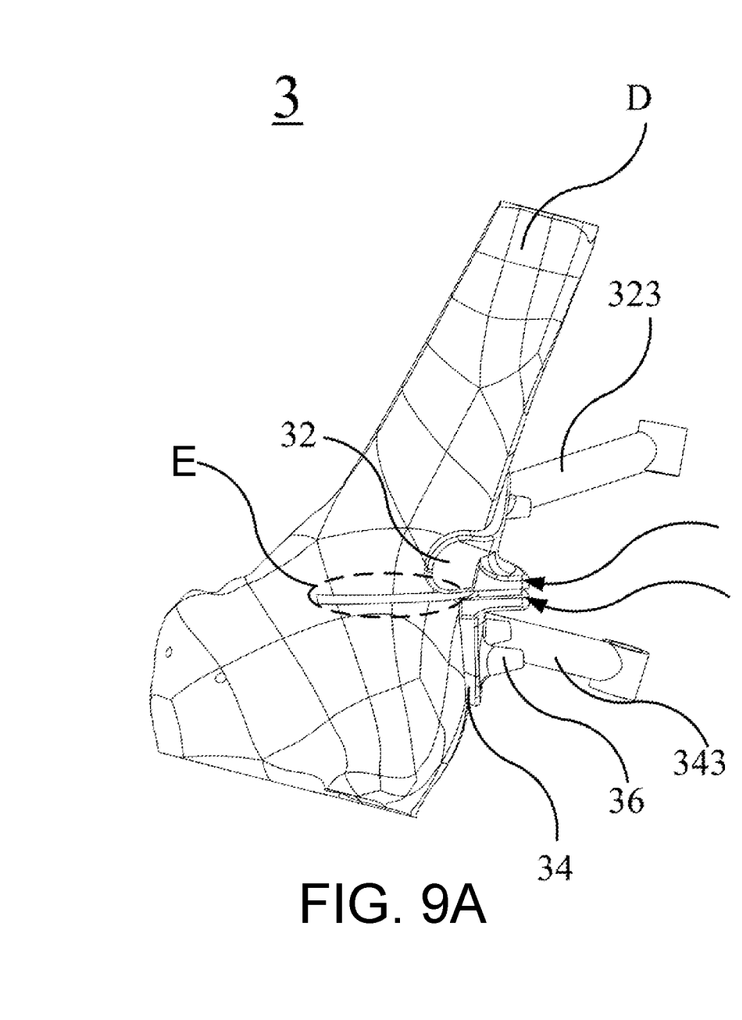
FIG. 9A illustrates a front view of the other embodiment of the present invention when implemented.
Figure 9B:
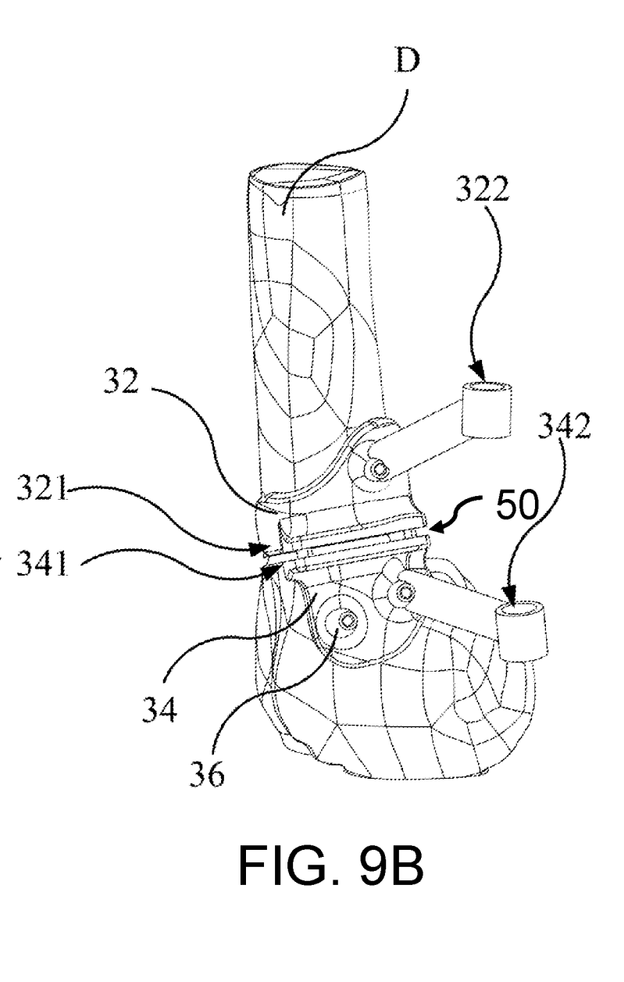
FIG. 9B illustrates a side view of the other embodiment of the present invention when implemented.

Please refer to FIG. 8A, FIG. 8B, FIG. 9A and FIG. 9B. FIG. 8A illustrates a side view of the other embodiment of the present invention when implemented. FIG. 8B illustrates the position at which the femur D is to be cut when the present invention is practiced. FIG. 9A illustrates a front view of the other embodiment of the present invention when implemented. FIG. 9B illustrates a side view of the other embodiment of the present invention when implemented.

The present invention further provides a surgery device for osteotomy 3 which can be used in various osteotomy, correction or reduction surgery. The surgery device for osteotomy 3 can be used for various bones of the human body, such as: tibia B, femur D, fibula, humerus, ulna, radius, clavicle, scapula, etc., but not limited to. In the present embodiment, it is applied to guide a saw blade to perform the distal femoral osteotomy (DFO) of a femur D. The surgery device for osteotomy 3 comprises: a first body component 32, a second body component 34 and a plurality of fixed slots 36. In this embodiment, the first body component 32 and the second body component 34 are connected by a connecting part. When the operation is performed, the surgeon can directly cut the connecting part with the bone saw, but not limited to. The first body component 32 and the second body component 34 can be directly used without using the connecting part. In addition, the first body component 32 and the second body component 34 may be connected in other forms. FIG. 8A to FIG. 9B shows the femur is the body's left thigh (femur) near the knee. However, the scope of application is not limited thereto, it can also be applied to other positions of other bones.

The aforementioned femur D is defined as a third cutting position C3 by the surgery device for osteotomy 3. Wherein the first body component 32 is disposed above the third cutting position C3 and has an upper guide edge 321 and a first correcting perforation 322, the first correcting perforation 322 is connected to the first body component 32 by a first bar 323. The second body component 34 is disposed below the third cutting position C3 or below the upper guide edge 321 and has a lower guide edge 341 and a second correcting perforation 342. The lower guide edge 341 is disposed below the upper guide edge 321. The second correcting perforation 342 is connected to the second body component 34 by a second bar 343. The surfaces of the first body component 32 and the second body component 34 have the plurality of fixed slots 36, and the surgery device for osteotomy 3 is fixed on the surface of the femur D by inserting a plurality of fixing pins and fixed bone needles 40 in the plurality of fixed slots 36.

Wherein the upper guide edge 321 and the lower guide edge 341 extend outwardly from the first body component 32 and the second body component 34, respectively. A guide groove 50 is formed between the upper guide edge 321 and the lower guide edge 341 for guiding the saw blade to the third cutting position C3. The upper guide edge 321 and the lower guide edge 341 are used to form the cutting track. The saw blade cuts the femur D according to the third cutting position C3, thereby operating the distal femoral osteotomy.

In the present invention, the first correcting perforation 322 and the second correcting perforation 342 are designed to confirm the angle at which the femoral opening is opened in the distal femoral osteotomy. For this reason, there is a regulative angle N between the first hole axis A1 of the first correcting perforation 322 and the second hole axis A2 of the second correcting perforation 342. In the distal femoral osteotomy, a gap of the osteotomy has a preoperative planning correction angle. When the femur D is opened by the first body component 32 and the second body component 34 with the correction angle, the first hole axis A1 of the first correcting perforation 322 and the second hole axis A2 of the second correcting perforation 342 can coincide. An alignment bar 20 is passed through the first correcting perforation 322 and the second correcting perforation 342 to ensure the correction angle. Firstly, the size of the aforementioned regulative angle N is based on the correction angle that the femur D needs to open in the distal femoral osteotomy. Secondly, the size of the regulative angle N is determined according to the desired correction angle and it is made. The alignment bar 20 can be inserted between the first correcting perforation 322 and the second correcting perforation 342 only when the femur D is opened at a preoperative planned correction angle by the first body component 32 and the second body component 34.

Please refer to FIG. 8A, FIG. 8B, FIG. 9A and FIG. 9B. Hereby explain how to use the present invention to perform the distal femoral osteotomy. In FIG. 8A and FIG. 8B, the surgery device for osteotomy 3 attached to the femoral position is located in the left thigh of human body and close to lateral distal end of the knee. However, the scope of application is not limited thereto, it can also be applied to other positions of other bones. In other words, the picture shows the positive side of FIG. 8A and FIG. 8B is pointing to the human body. The left side of FIG. 8A and FIG. 8B points to the front of the human body.

The present invention of the surgery device for osteotomy 3 is based on the femoral image information provided by patients with degenerative joint disease before surgery. The model of femur D was established using computer software. The position of the third cutting position C3 is determined according to the model of femur D. The overall structure of the surgery device for osteotomy 3 is tailored. Wherein the surgery device for osteotomy 3 is designed to be able to fully fit the surface of the patient's femur D, and then the three-dimensional printing technique is used to construct an integrally formed or combined solid instrument.

Please refer to FIG. 9A, the figure shows the completed cutting track E on the third cutting position C3. When the surgery device for osteotomy 3 is arranged on the surface of patient's femur, the surgeon inserts the saw blade and starts cutting according to the third cutting position C3 guided by the upper guide edge 321 and the lower guide edge 341 of the surgery device for osteotomy 3. The surgeon can use the upper guide edges 321 and the lower guide edges 341 as a reference for the calculation of the depth of cut. In another way, make a mark on the saw blade, you can use the naked eye to confirm whether the depth of the saw blade cut into the femur D reached the preset depth.

The saw blade is cut to a predetermined depth and cut along the upper guide edge 321 and the lower guide edge 341. Then, it cut off part of the femur D. The third cutting position C3 of the femur D is opened to the correction angle of preoperative planning in the case where the surgery device for osteotomy 3 is fixed to the femur D. The alignment bar 20 is then inserted through the first correcting perforation 322 and the second correcting perforation 342. After confirming the correction angle of the surgical incision of the femur D, the gap can be fixed to complete the operation.

In summary, the present invention provides a surgery device for osteotomy 1, 2, 3. In one embodiment, it is tailored to the skeletal image information collected from patients with degenerative joint disease before surgery. In one embodiment, the first cutting position C1 is designated by the upper guide edge 122, 222 and the lower guide edge 141, 241 as a reference point for the cutting depth. So that the surgeon can easily control the cutting depth. And the second cutting position C2 is designated by the side guide edge 121, 221 for operation. In another embodiment, the third cutting position C3 is designated by the upper guide edge 321 and the lower guide edge 341 as a reference point for the cutting depth. So that the surgeon can easily control the cutting depth. The present invention can avoid ligament injury during surgery. It can also cut out to resist the rotation of the bones due to the movement. The present invention is designed according to a preoperative correction plan so that the surgical procedure can be simplified.

Compared with the conventional technique, the surgery device for osteotomy 1, 2, 3 is manufactured by three-dimensional printing according to the patient's skeletal data collected before the operation and evaluating the optimal surgical cutting position. The device itself can fit the patient's bones fully. The surgeon can perform the first cutting position C1 or the third cutting position C3 under the guide groove 50 specified by the device. The guide groove 50 allows the surgeon to perform the operation accurately. It also provides a reference for calculating the angle and depth of cutting. The side guide edge 121, 221 provides the surgical reference of the surgeon at the second cutting position C2. In addition to improving the surgery itself, the present invention also standardizes the implementation of the surgeon's operation.

The foregoing descriptions are preferred embodiments of the present invention. As is understood by a person skilled in the art, the aforementioned preferred embodiments of the present invention are illustrative of the present invention rather than limiting the present invention. The present invention is intended to cover various modifications and similar arrangements included within the spirit and scope of the appended claims, the scope of which should be accorded the broadest interpretation so as to encompass all such modifications and similar structures.

We claim:

1. A surgery device for osteotomy comprising:
   a first body component having a side guide edge and an upper guide edge for forming a cutting track;
   a second body component having a lower guide edge disposed below said upper guide edge, a guide groove being formed between said upper guide edge and said lower guide edge for guiding a saw blade to perform a cutting procedure;
   wherein said upper guide edge has a first correcting perforation, said lower guide edge has a second correcting perforation; wherein a regulative angle between a first hole axis of said first correcting perforation and a second hole axis of said second correcting perforation is formed, when an open angle of gap of osteotomy is the same as that of a preoperative planning correction angle, said first hole axis of said first correcting perforation and said second hole axis of said second correcting perforation will coincide, such that an alignment bar can be inserted between said first correcting perforation and said second correcting perforation.

2. The surgery device for osteotomy of claim 1, further comprising:
   a fixing component engaging said first body component and said second body component so that said first body component and said second body component are combined to ensure a sufficient area to attach the surface of a bone.

3. The surgery device for osteotomy of claim 1, the surfaces of said first body component and said second body component having a plurality of fixed slots, said surgery device for osteotomy being fixed on the surface of said bone by inserting a plurality of fixing pins and fixed bone needles in said plurality of fixed slots.

* * * * *